United States Patent [19]

von Alfthan et al.

[11] 4,278,885

[45] Jul. 14, 1981

[54] APPARATUS FOR MEASURING THE CONCENTRATIONS OF ELEMENTS IN A MATERIAL BY THE CAPTURE GAMMA METHOD

[75] Inventors: Georg C. von Alfthan, Espoo; Tuula A. Lukander, Kauniainen; Pekka Rautala, Espoo; Heikki J. Sipilä, Espoo; Seppo J. Uusitalo, Espoo, all of Finland

[73] Assignee: Outokumpu Oy, Helsinki, Finland

[21] Appl. No.: 35,245

[22] Filed: May 2, 1979

[30] Foreign Application Priority Data

May 4, 1978 [FI] Finland .................................. 781381

[51] Int. Cl.³ .............................................. G01T 1/22
[52] U.S. Cl. ............................... 250/370; 250/358 R; 250/390; 250/435
[58] Field of Search ........... 250/253, 302, 303, 358 R, 250/390, 391, 392, 435 R, 370

[56] References Cited

U.S. PATENT DOCUMENTS

| | | | |
|---|---|---|---|
| 2,938,119 | 5/1960 | McKay | 250/390 |
| 3,723,727 | 3/1973 | Wogman et al. | 250/253 |

Primary Examiner—Davis L. Willis
Attorney, Agent, or Firm—Brooks, Haidt, Haffner & Delahunty

[57] ABSTRACT

The invention provides an apparatus for measuring the concentrations of elements in a material sample by the capture gamma method, said apparatus including a neutron source in the form of an isotope source or a neutron generator, a moderator surrounding the neutron source and being at least partly constituted by heavy water, a semiconductor detector serving as gamma radiation detector and positioned in the immediate vicinity of the material to be analyzed and in the flux of slow neutrons, so much of the moderator being provided before the detector that this is reached only by a very low number of fast neutrons that have a damaging effect upon the detector. The material itself can form part of the moderator and also graphite is preferably used as a moderator around said heavy water. Furthermore, a body of bismuth having the shape of a cone or a double cone is preferably positioned in front of the neutron source so as to absorb gamma radiation and to scatter fast neutrons.

16 Claims, 8 Drawing Figures

APPARATUS FOR MEASURING THE CONCENTRATIONS OF ELEMENTS IN A MATERIAL BY THE CAPTURE GAMMA METHOD

BACKGROUND OF THE INVENTION

1. Field of the Invention

The present invention relates to an apparatus for measuring the concentrations of elements in a material by the capture gamma method, the apparatus comprising a neutron source, a gamma-radiation detector, and a moderator between these two.

DESCRIPTION OF THE PRIOR ART

The capture gamma method is known per se. In this method the neutrons traveling from a neutron source are allowed to be captured by the atom nuclei of the specimen, whereby energy is released in the form of gamma-radiation. The elements present in the specimen can be identified and their concentrations calculated on the basis of the energies and intensities of the gamma-radiation.

The capture gamma method has been studied over a long period of time, and it has been applied by using various neutron sources, such as reactors, neutron generators and isotope sources. The neutrons traveling from the source are fast, and they must be decelerated in a moderator before they cause nuclear reactions which produce capture gammas. The deceleration is best performed in a substance with lightweight atom nuclei (hydrogen). The energies and intensities of the gamma-radiation generated are detected by gamma-ray spectroscopy, and the elements and their concentrations can be determined on the basis of these energies and intensities.

The most important advantage of the capture gamma method is that the penetration depth of both neutrons and gamma-radiation is great in the specimen. For example, the half-value thickness of the feed mixture of a flash-smelting furnace is approximately 6 cm for neutrons and approximately 12 cm for gamma-radiation. The half-value thickness for neutrons can vary considerably from one specimen to another. Usually the absorption of gamma-radiation is dependent on only the thickness of the specimen. The specimens are usually very coarse-grained. The measuring can also be performed through a thick aluminum plate. The measuring can be performed directly from a process pipe, silo, or conveyor.

If the specimen bed is sufficiently thick, the detector and the source can be placed on different sides of the specimen, thus creating a greater distance between them, which is advantageous in terms of protecting the detector. Using a thicker specimen, however, a large portion of the capture gammas have to pass through the entire specimen layer, thereby increasing the Compton background in the spectrum, and it is more advantageous to use a geometry in which the detector and the source are on the same side of the specimen.

According to the literature, the capture gamma method has been used as a continuous-working process only with a scintillation detector. A semiconductor detector has been used in intermittent measurements in, for example, bore analysis. This is so because fast electrons damage the semiconductor detector even in rather small quantities (less than $10^{10}$ neutrons/cm$^2$). For example, in the analysis of a flash-smelting furnace feed, a better resolution of a semiconductor detector is, however, necessary in order to make distinction between the lines of various substances. Thus, the problem is to obtain a sufficient quantity of thermal neutrons in the sample and at the same time to prevent fast neutrons from entering the detector. The detector must be so close to the specimen that the capture gamma quanta can be detected effectively.

SUMMARY OF THE INVENTION

The present invention provides an apparatus of the character once described, which comprises:
a neutron source,
a moderator surrounding the neutron source and being at least partly constituted by heavy water,
a gamma radiation detector in the form of a semiconductor detector, said detector being positioned close to or inside the material to be measured and in the flux of slow neutrons, there being so much of the moderator between the neutron source and the material-detector combination that at the most only a few fast neutrons can reach the detector.

It is an object of the present invention to solve the above problem and to provide a measuring apparatus with which capture gamma measuring can be performed on a continuous-working basis and with a high capacity.

Essential in the invention is the using of heavy water as the moderator to obtain a large flux of slow neutrons in the sample and at the same time so small a flux of fast neutrons that the detector can be placed right next to or inside the specimen. Thereby the gamma-radiation emitted by the specimen can be measured with a high efficiency.

Before describing the invention in detail it is advisable to discuss the principles of the theory underlying the invention.

The deceleration and diffusion of the neutrons in a mathematically difficult problem for which a precise solution can be found only by means of a very simple geometry, for example in a case of spherical symmetry. The measuring equipment includes, however, many different materials and interfaces with various directions. The simplest solution in this case is to use the Monte Carlo method in the calculations, which is based on the knowledge of the laws of probability governing the behavior of an individual neutron in each medium. By following several different neutron case histories (travel of a neutron decelerating and changing direction upon impinging against atoms, and finally absorption), an idea of the number and energy distribution of neutrons in various places is gradually obtained.

In connection with the present invention, calculations concerning different capture gamma measurement arrangements were carried out by the Monte Carlo method and it was discovered that the use of slightly absorbing decelerating substances (heavy water, graphite) is essential. The suitable geometries were also discovered, and the test performed showed that the results of simulation calculations were right.

DESCRIPTION OF THE PREFERRED EMBODIMENTS

Figure 1:
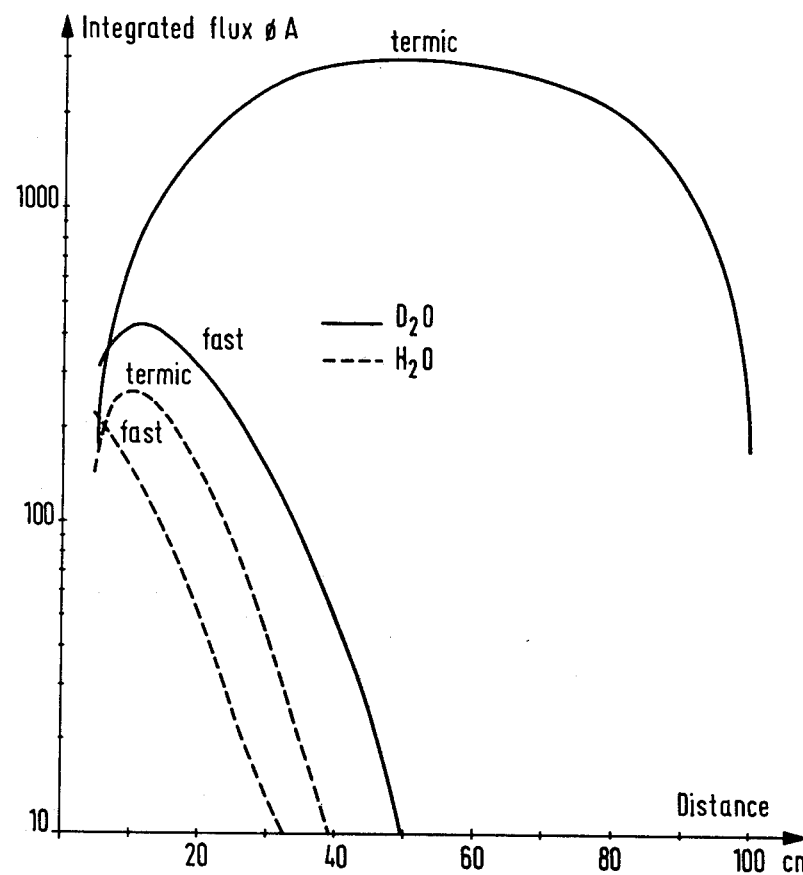
FIG. 1 depicts curves connected with the explanation of the theory of the invention.

The results shown in FIG. 1 were obtained by calculating the thermal and the fast flux on the basis of $H_2O$ and $D_2O$ spheres with a radius of 100 cm. The figure shows that in $H_2O$ the thermal flux drops at the same rate as the fast flux, whereas in $D_2O$ the diffusion spreads the thermal flux over a larger area without absorption and only leakage outside the sphere begins to reduce the flux.

The deceleration distance of graphite is greater and the diffusion distance smaller than those of $D_2O$, but because of its low price graphite is advantageous to use around $D_2O$, and possibly $H_2O$ around the graphite. In order to scatter the fast neutrons traveling towards the detector and in order to absorb the gammas of the source, it is advantageous to use a Bi cone between the source and the detector. Bismuth has hardly any interfering capture gammas and it is a heavy material.

Used with a semiconductor detector, however, bismuth is a very poor decelerator, and it must not extend as far as the detector lest the fast neutrons travel to the detector along it. The table below shows the quantity (n) of neutrons arriving at the detector within a certain time period in arrangements according to FIG. 2. The $D_2O$ distance does not have a very great effect, but a longer distance is somewhat better. A broader initial cone further improves the situation. It scatters the neutrons in a larger space angle.

TABLE 1

|   | A | B | C | D |   |
|---|---|---|---|---|---|
| a | 10 | 20 | 10 | 20 | (cm) |
| b | — | — | 10 | — | (cm) |
| l | 50 | 50 | 50 | 50 | (cm) |
| n | 147 | 131 | 168 | 113 |   |

Figures 2A, 2B, 2C, 2D:
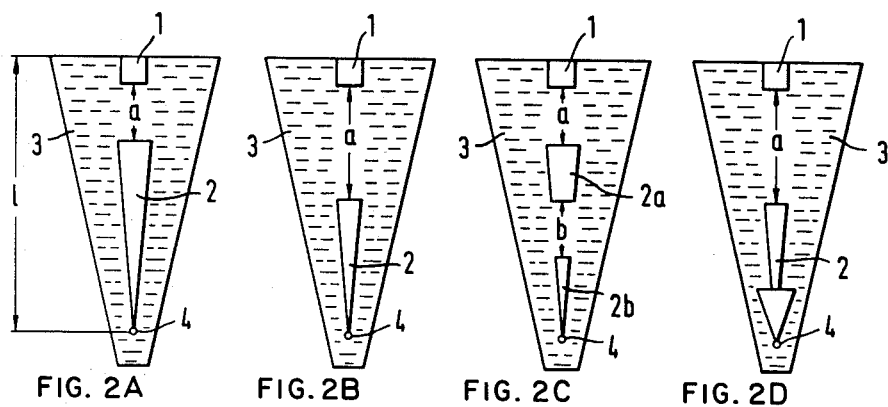
FIG. 2 depicts various alternatives of the bismuth radiation shield.

In FIG. 2 reference numeral 1 indicates the detector, which can be, for example, a semiconductor detector. Numeral 2 indicates the scattering cone, which is of bismuth, for example. Around the scattering device there is, conically enclosed, heavy water 3. Numeral 4 indicates the source of radiation.

Heavy water is rather expensive and therefore its quantity is worth optimizing. The geometry according to FIG. 3 has been arrived at as a result of optimization. In this geometry most of the decelerator is graphite instead of heavy water. However, it is advantageous to use heavy water on the side facing the detector, since it is essential that the neutrons arriving at the detector have already thermalized. The width of the necessary $D_2O$ space has been calculated, and it has been observed that increasing the quantity of $D_2O$ beyond approx. 12 liters no longer substantially improves the situation.

Figure 3:
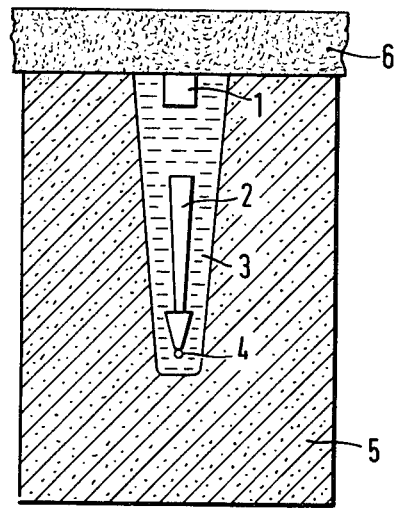
FIG. 3 depicts one measuring arrangement which has proven to be especially advantageous.

In FIG. 3 reference numerals 1, 2 and 3 indicate, as above, the detector, the scattering device, and the heavy water around the scattering device. The neutron source 4 is situated at the apex of the scattering device, numeral 5 indicates the graphite, and numeral 6 the material on which the measuring is performed, situated on a conveyor, for example.

The neutron source used in the experiments and calculations is a $^{252}Cf$-isotope source because it produces the best neutron yield per activity unit, its price is rather advantageous and its neutron spectrum is soft. Other isotope sources or neutron generators can, of course, also be used.

In the literature, data concerning the quantity of fast neutrons tolerated by the detector vary to a rather high degree. Here $10^9$ n/cm$^2$, which represents a cautious average, has been taken as a starting point. On the basis of simulation, an increase of 15 cm in the distance between the source and the detector decreases the dose of fast neutrons to one-tenth. The values obtained for the useful life of the detector with the optimal geometry using different distances were those according to Table 2 for 20 $\mu$g $^{252}Cf$:

TABLE 2

| Effect of distance on the useful life of detector and gamma intensity | | |
|---|---|---|
| Distance | Useful life of detector | Relative gamma intensity |
| 45 cm | 110 days | 2.2 |
| 55 cm | 1.4 years | 1.2 |
| 60 cm | 3 years | 0.8 |
| 65 cm | 6.3 years | 0.5 |

Most likely it is advantageous to use a distance of approx. 65 cm in the construction, although in the experiment it was 55 cm. A damaged detector is not unusable but can be repaired by the manufacturer.

Figure 4:
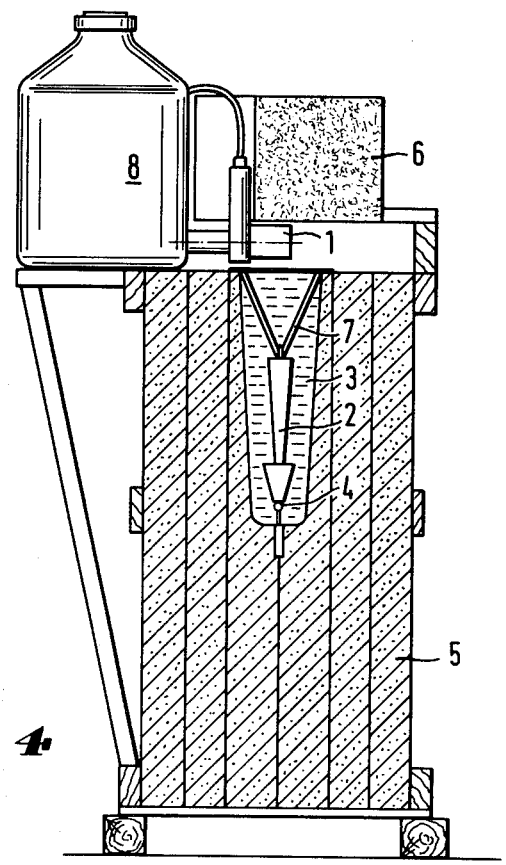
FIG. 4 depicts one measurement arrangement.

The experimental geometry according to FIG. 4 was obtained on the basis of the optimization performed.

In FIG. 4, reference numerals 1–6 indicate the same parts as above. Numeral 7 indicates a support device, which keeps the scattering device 2 in the correct position. Numeral 8 indicates the liquid nitrogen bottle; liquid nitrogen is used for maintaining the detector at a low temperature. A hollow has been made in the specimen tank 6 for the preamplifier of the detector. It should be noted that this arrangement was made for a laboratory experiment and that in practical applications the arrangement can considerably differ from this one.

The equipment available for the experiments included a Ge(Li) detector (volume 110 cm$^3$, effectiveness 21.8%) and a data machine system coupled to it. The results were obtained in the form of a listing on punch tape and a plotter. The source used 1 $\mu$g $^{252}Cf$. The measuring period was 100 min and the specimens were Ni and Cu concentrates. The concentrations of the principal components of the concentrates are given in Table 3.

TABLE 3

| Concentrations of the principal components of the concentrates | | | | | |
|---|---|---|---|---|---|
|   | Ni % | Cu % | S % | Fe % | SiO$_2$ % |
| Ni concentrate | 5.52 | 3.40 | 23.3 | 29.8 | 24.9 |
| Cu concentrate | 0.21 | 24.8 | 29.6 | 29.8 | 8.3 |

In addition, background measurements were performed by replacing the specimen with a boric acid solution having a reflection capacity to thermal neutrons approximately equal to that of the specimen. The geometry for the measuring is shown in FIG. 4. Furthermore, the geometry was varied so that the empty space surrounding the detector between the sample and the moderator was filled with specimen and in other cases graphite pieces were fitted as reflectors around the detector. In addition experiments were performed on the effects on the spectrum of a thin Cd plate placed to protect the detector. The relatively great height of the apparatus shown in FIG. 4 is due to the fact that the graphite was in standard-length bars.

The program used for the processing of the spectrum was a program called Vipunen developed in the Department of Physics, University of Helsinki. On the basis of international testing this is a very good program for processing the spectrum. The program detects the peaks, calibrates the energies, determines the background, and calculates the area of the peaks and their error values. The listing gave, in addition to the spectrum, a table of the peaks and their parameters.

The most important peaks of the various substances were used in estimating the error caused by pulse statistics:

Fe: 7.646 MeV and 7.632 MeV with escape peaks
S: 5.420 MeV with escape peaks, 3.221 MeV, 2.931 MeV and 2.380 MeV
Cu: 7.915 MeV and 7.306 MeV with escape peaks
Ni: 8.999 MeV and 8.535 MeV with escape peaks
Si: 4.934 MeV and 3.539 MeV.

The results obtained with Ni concentrate are shown in the table below.

TABLE 4

| Source 1 μg $^{252}$Cf, measuring period 100 min | | |
|---|---|---|
| | Ni concentrate | |
| | relative error % | absolute error % |
| S | 4.1 | 0.96 |
| Fe | 1.8 | 0.54 |
| Cu | 9.0 | 0.31 |
| Ni | 4.5 | 0.25 |
| SiO$_2$ | 11.5 | 2.9 |

Corresponding results would be obtained by using 10 μg/10 min or 20 μg/5 min. By quadrupling the time, the error could be reduced by one half.

Figure 5:
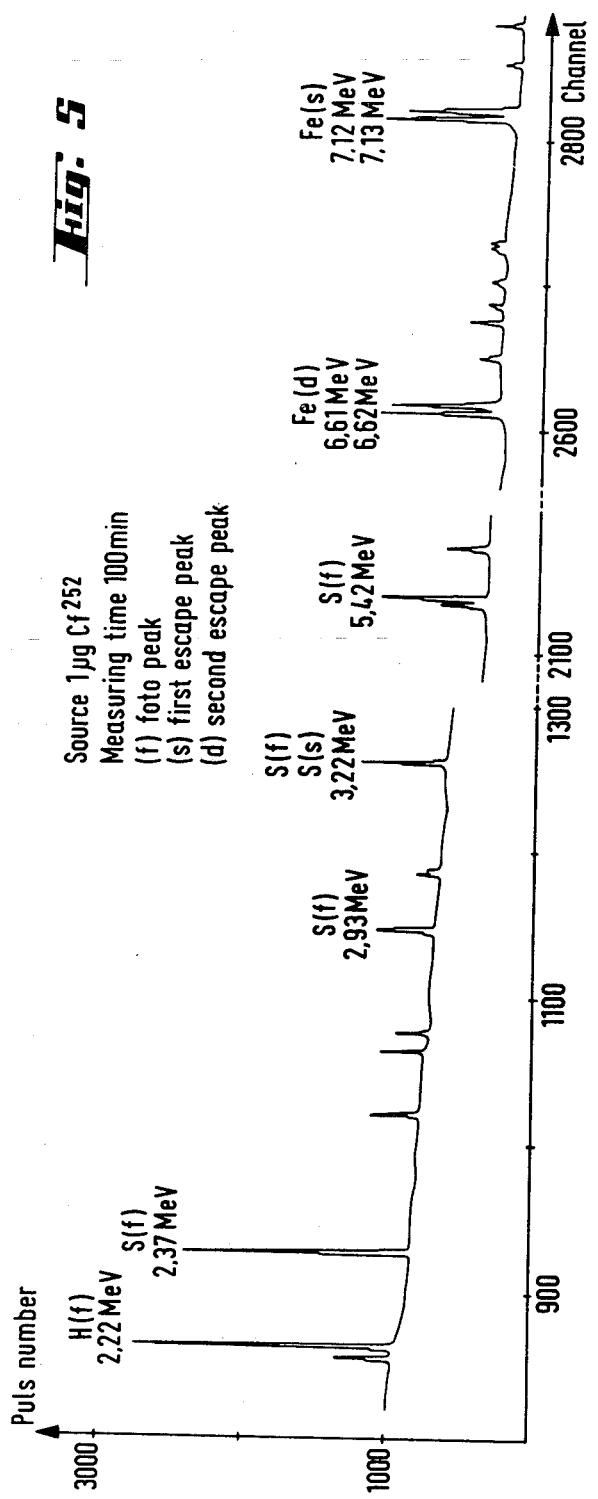
FIGS. 5 and 6 depict spectra measured using the apparatus according to the invention.
Figure 6:
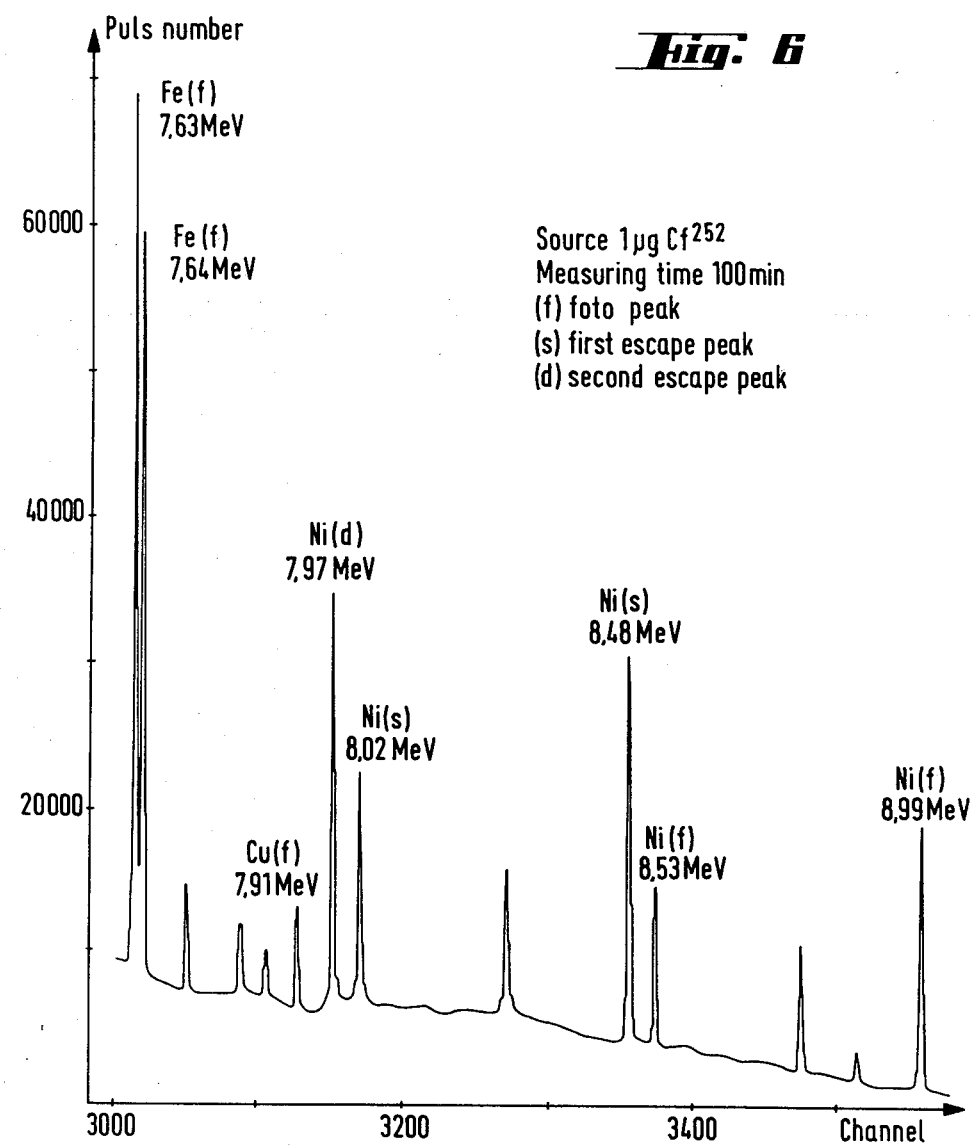

FIGS. 5 and 6 show parts of the spectrum of Ni concentrate.

The capture gammas and activation peaks produced by the structure material of the detector could be eliminated using a Cd shield. Some neutron absorber other than Cd could worsen the peak-background ratio to a lesser degree. The quantity of capture gammas obtained from the specimen was reduced by 1.7 when using a Cd shield.

Figure 7:
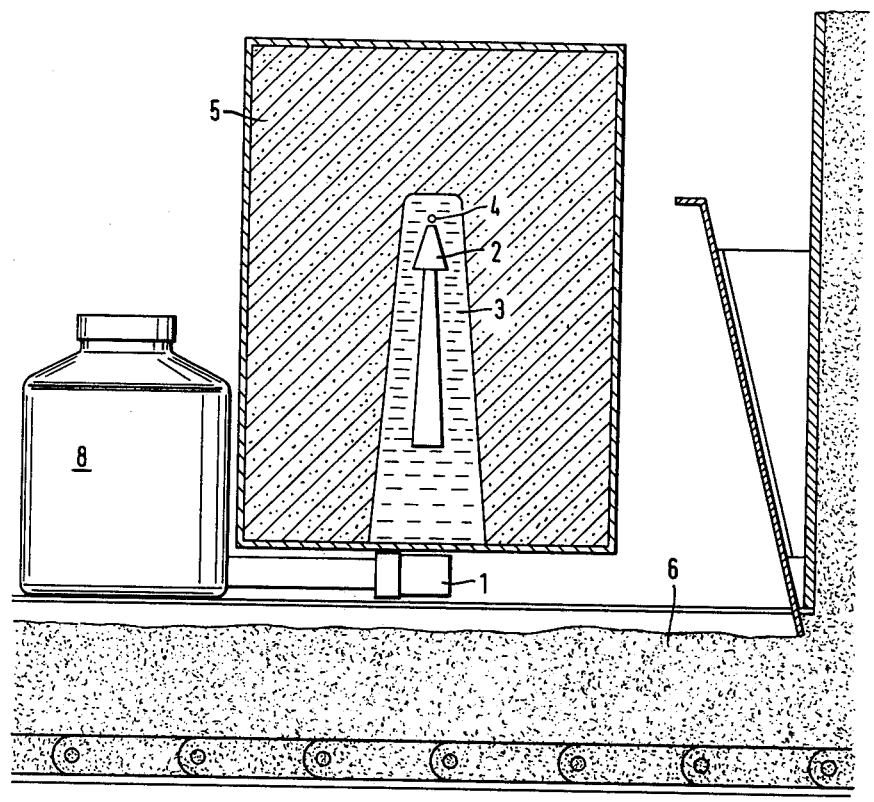
FIG. 7 depicts another, slightly modified measuring arrangement.

Finally, FIG. 7 shows how a measuring apparatus according to the invention could be positioned for the measuring of, for example, material 6 being conveyed on a Reedler conveyor. The geometry is the same as that shown in FIGS. 3 and 4, but it has been reversed.

Figure 8:
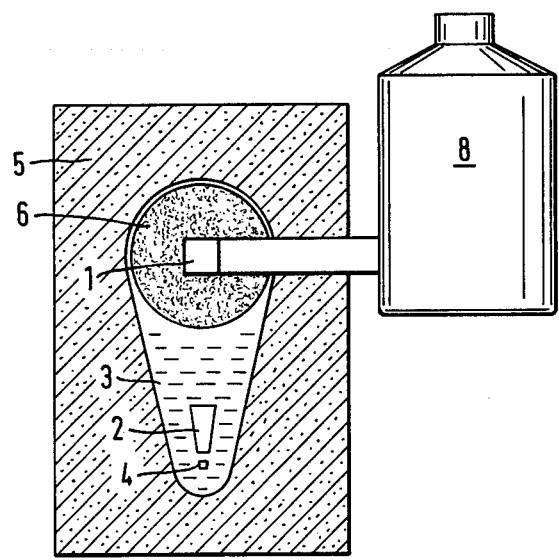
FIG. 8 depicts the application of the apparatus to the measurement of a slurry.

It is evident that the geometry can be varied in many ways without deviating from the idea of the invention, which is using heavy water as moderator. If, for example, the material to be studied is a flow of material in a pipe, e.g. a slurry, it also works as a moderator itself. The detector can be placed in the slurry, in which case the arrangement will be similar to that shown in FIG. 8. In this case the specimen to be studied, i.e. slurry 6, flows in a pipe and the detector is in the middle of the pipe. Naturally, several other alternatives are also possible.

What is claimed is:

1. An apparatus for measuring the concentrations of elements in a material by the capture gamma method, said apparatus comprising
   a neutron source,
   a moderator surrounding the neutron source and being at least partly constituted by heavy water,
   a gamma radiation detector in the form of a semiconductor detector, said detector being positioned close to the material to be measured and in a flux of slow neutrons, there being so much of the moderator between the neutron source and the detector that at most only a few fast neutrons can reach the detector.

2. An apparatus according to claim 1, wherein part of the moderator is graphite.

3. Apparatus according to claim 2 wherein the graphite is situated around the heavy water.

4. An apparatus according to claim 1 or 2, further comprising as moderator substance ordinary water.

5. An apparatus according to claim 1, wherein a heavy substance which absorbs neutrons only slightly is placed between the neutron source and the detector to absorb gamma-radiation and to scatter fast neutrons.

6. An apparatus according to claim 5, wherein the scattering substance has the shape of a cone, the neutron source being situated in the vicinity of the cone apex, and the base of the cone facing the detector.

7. An apparatus according to claim 5, wherein the distance between the scattering substance and the semiconductor detector in heavy water is at least about 10 cm.

8. Apparatus according to claim 5 wherein the heavy substance is bismuth.

9. Apparatus according to claim 5 wherein the scattering substance has the shape of two cones in succession, the neutron source being situated in the vicinity of the apex of one of the cones, and the base of the other cone facing the detector.

10. An apparatus according to any of claims 1, 2, 5 or 6, wherein the intensity of the neutron source is about 5.10$^7$ neutrons/s, the distance between the neutron sourse and the detector is at least about 45 cm, this distance increasing by about 15 cm when the intensity increases by one decade.

11. Apparatus according to claim 10 further comprising as moderator substance ordinary water.

12. An apparatus according to any one of claims 1, 2, 5, or 6, wherein the intensity of the neutron source is about 5.10$^7$ neutrons/s, the distance between the neutron source and the detector is at least about 45 cm, this distance increasing by about 15 cm when the intensity increases by one decade, and wherein the heavy water has been arranged around the neutron source, substantially in the form of a truncated cone, the neutron source being situated at the narrow end of the cone and the detector being situated at the wider end of the cone.

13. Apparatus according to claim 12 further comprising as moderator substance ordinary water.

14. An apparatus according to claim 1, wherein the material to be studied flows in a pipe, the detector being positioned inside the pipe in the flowing material, which itself partly serves as a moderator.

15. An apparatus according to claim 1, wherein the neutron source is an isotope source.

16. An apparatus according to claim 1, wherein the neutron source is a neutron generator.

* * * * *